United States Patent [19]

Jones, Jr. et al.

[11] Patent Number: 4,924,853

[45] Date of Patent: May 15, 1990

[54] STEREOSCOPIC MEDICAL VIEWING DEVICE

[75] Inventors: Edwin R. Jones, Jr., Columbia; A. Porter McLaurin, Chapin, both of S.C.

[73] Assignee: Medical Dimensions, Inc., Columbia, S.C.

[21] Appl. No.: 354,761

[22] Filed: May 22, 1989

[51] Int. Cl.$^5$ .............................................. A61B 1/04
[52] U.S. Cl. ......................................... 128/6; 358/98
[58] Field of Search ........................... 128/4, 6; 358/98

[56] References Cited

U.S. PATENT DOCUMENTS

| | | | |
|---|---|---|---|
| 3,067,648 | 11/1962 | Cohen | 128/6 X |
| 3,994,557 | 11/1976 | Hopkins | 128/4 X |
| 4,061,135 | 12/1977 | Widran et al. | 128/6 |
| 4,259,948 | 4/1981 | Urban | 128/6 |
| 4,413,278 | 11/1983 | Feinbloom | 358/98 X |
| 4,429,328 | 1/1984 | Jones et al. | 358/88 |
| 4,528,587 | 7/1985 | Jones, Jr. | 358/92 |
| 4,576,147 | 3/1986 | Hashiguchi | 128/6 |
| 4,589,404 | 5/1986 | Barath et al. | 128/6 |
| 4,590,923 | 5/1986 | Watanabe | 128/6 |
| 4,651,201 | 3/1987 | Schoolman | 358/98 |
| 4,656,508 | 4/1987 | Yokota | 358/98 |
| 4,836,188 | 6/1989 | Berry | 128/6 |

OTHER PUBLICATIONS

"The Binocular Microscope", F. Jentzsch.
*The Microscope*, by H. Gazu, pp. 32-35.

Primary Examiner—William H. Grieb
Attorney, Agent, or Firm—Foley & Lardner, Schwartz, Jeffery, Schwaab, Mack, Blumenthal & Evans

[57] ABSTRACT

The invention concerns an endoscopic instrument having a three-dimensional optical viewing system. Images from an interior body region are transmitted through image transmission elements contained within the endoscope probe to a prism arrangement. The prism maintains the images in upright position regardless of the rotation of the instrument. A shutter system operating at a predetermined frequency alternately opens and closes the optical path of each image. These images are converted to electrical pulses in accordance with the requirements of the three-dimensional television system used to display an image of the body region.

16 Claims, 3 Drawing Sheets

STEREOSCOPIC MEDICAL VIEWING DEVICE

BACKGROUND OF THE INVENTION

This invention relates to an arthroscope for viewing the internal structure or condition of a human or animal joint. Arthroscopes belong to a class of medical instruments, called endoscopes, that enable physicians to examine, or perform surgery on, various organs and interior body cavities.

Arthroscopes utilize a thin, elongated probe for insertion into or near the region or joint to be examined. Light is transmitted to the inserted (distal) end of the probe, to illuminate the region under observation. An image transmission device, using this light, transmits to the observing physician a view of the region.

A light tube or optic fiber bundle is conventionally used to illuminate the region being observed. If an optic fiber bundle is used, an incoherent bundle will suffice. Transmission of an image from the observed region to the observer, however, requires a coherent bundle. The distal end of the instrument is covered by a lens, which focuses images to be viewed on the ends of the optic fibers in the bundle or transmits these images to a glass image transmission rod.

Arthroscopes are usually equipped with irrigation passages for supplying cleaning liquid to the outside distal end of the probe and keeping it clear for viewing. Air is sometimes also supplied through passages in the probe for the same purpose. In addition, surgical tools can be inserted into an interior body region through an arthroscope probe.

Arthroscopic optical systems began with simple devices in which physicians looked straight ahead through an eye piece. These early instruments were hard to use, however, significantly slowing down the examination and making surgery difficult. A thorough inspection of the interior region required the probe to be wiggled while inserted in the body. Today, however, arthroscopic design has progressed to the stage where the image is displayed on a television monitoring screen.

While these modern arthroscopic systems represent great advances in medical instrumentation and technology, they still suffer from some shortcomings. Principal among these is the lack of realistic three-dimensionality in the image produced by the arthroscope.

SUMMARY OF THE INVENTION

It is an object of the invention, therefore, to provide a medical instrument through which an interior body region can be viewed three-dimensionally.

It is another object of the invention to provide a medical instrument through which a 360° view of an interior body region can be obtained, while the view remains continually in an upright position.

Still another object of the invention is to provide a method for viewing a three-dimensional image of an interior body region, whereby visual images of the region are converted to electrical signals and displayed on a television screen.

The present invention for achieving these and other objects is an arthroscope in which optically conductive fiber bundles, glass rods, or their equivalents, transmit light through the probe to its distal end, to illuminate the interior body region under observation. A pair of parallel or side-by-side image transmission elements, also contained within the probe, transmit the observed image to the viewing end of the instrument. While various kinds of coherent light transmission elements may be used for image transmission, glass rods lend themselves especially well to the very small diameters of arthroscope probes.

The side-by-side image transmission elements may terminate at the distal end of the probe at an angle of between 25° and 30° away from the longitudinal axis of the probe. The distal end of the probe terminates at the same angle, to guard against any blocking of the images received by the image transmission elements.

As the arthroscope rotates, therefore, the viewer continually sees new areas of the region. This view, as provided by the image transmission elements is directed or tilted to the side, i.e., away from the longitudinal axis of the probe, at an angle of between 25°–30°; i.e., at the same angle at which the ends of the light transmission elements and the probe are terminated. As will be explained, two parallel image transmission elements are necessary to obtain the desired three dimensional effect.

The fields of view of the image transmission elements are ordinarily fixed to converge at a distance of about 2.5 cm from their distal ends, although this convergence may be varied. The images are optically transmitted by the image transmission elements to a prism system, rotatable with the probe. This synchronous rotation of the prism system and the image transmission elements maintains the view of the observed region upright, regardless of the amount of rotation.

It is conventional to merge the images along a common optical axis (the longitudinal axis of the probe), for direct observation by the physician. Prismatic systems are often used for this purpose. The merged image is viewed by looking through a collimating eye piece or compound lens arrangement. In this invention, however, the optical images of the viewed region are converted to electrical signals by a photo-detector or its equivalent. These electrical signals are used to produce three-dimensional images on a television screen.

As will be explained, images from each image transmission element (upon conversion to electrical signals) are not simultaneously transmitted to the signal input circuitry of the television monitor. Rather, they are sequentially transmitted, this sequential transmission being controlled by shutters within the prism system.

Such sequential transmissions of the electrical images may be achieved by a particular interlacing of images from each image transmission element, as described in U.S. Pat. No. 4,528,587, to Jones, a co-inventor of this invention, or by the alternating transmission of images from each image transmission element, as in U.S. Pat. No. 4,429,328, to Jones, McLaurin and Cathey, the first two of whom are the joint inventors of this invention.

In order to achieve the optimal three-dimensional effect in the television presentation of the observed region, the switching rate between images is selected in accordance with the teachings of these patents. It is also explained in each patent how the switching rate can be set to take into account the 60 Hertz cathode ray beam sweep rate used for commercial television broadcasting.

DETAILED DESCRIPTION OF THE PREFERRED EMBODIMENTS

The invention includes an arthroscope and associated television system for viewing in three dimensions the interior of a body part or region, and a method for producing these views on a television screen.

Figure 1:
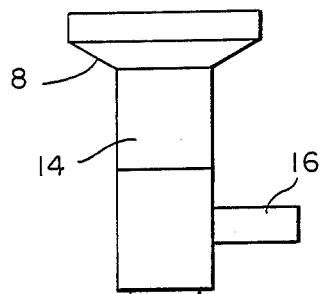
FIG. 1 is a side elevation view of a prior art arthroscope.

Referring to FIG. 1, the arthroscope 2 includes an elongated hollow probe 4, of tubular form, having a distal end 6. The probe contains two parallel or side-by-side image transmission elements. These elements transmit to the user of the instrument images of the region or body part under observation.

The viewing (user's) end of the arthroscope includes a prismatic arrangement 12 (FIG. 3) contained in a housing 14 (FIG. 1). This prismatic arrangement is positioned in the optical path between the viewing ends of the image transmission elements and the collimating lens 10. The lens 10 is coupled to the prism system through optical coupling section 8, of conventional design.

A light entry port 16 is optically connected to the probe, to provide viewing light at the distal end of the arthroscope. Usually, this is done by use of optic fiber bundles extending through passages or tubes within the probe. In addition, the arthroscope may contain other conventional components, including fluid ports for cleaning the distal region and laser scalpels or other instruments.

Attention is directed to the prior art for illustration and explanation of these conventional features. This prior art is exemplified by U.S. Pat. Nos. 4,651,201, to Schoolman; 4,590,923, to Watanabe; 4,061,135, to Widran et al and 4,413,278 to Feinbloom.

Figure 2:
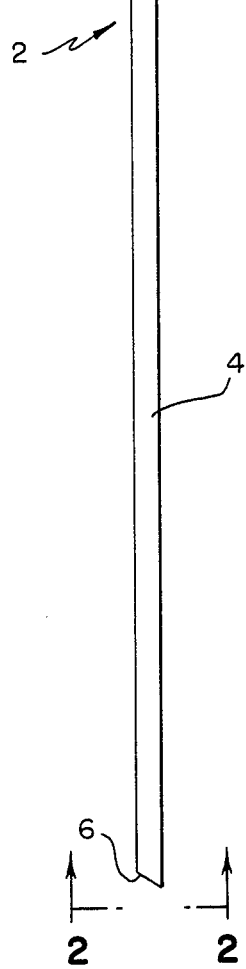
FIG. 2 is a greatly enlarged transverse end view of the distal end of the arthroscope used in this invention, taken along lines 2—2 of FIG. 1.
Figure 2:
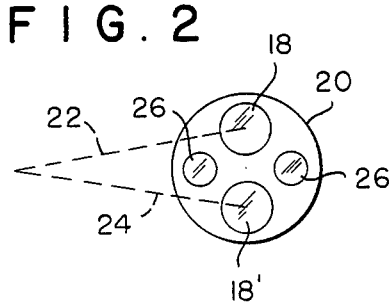

FIG. 2, taken along lines 2—2 of FIG. 1, depicts the distal end of the arthroscope. The two image transmission elements 18 and 18, are also contained within a tube 20. The tube 20 is, in turn, contained within probe 4. Other physical arrangements, as known in the prior art, could alternatively be used. These image transmission elements are optically coupled to the prismatic arrangement 12.

The image transmission elements 18 and 18' may vary in diameter, but diameters of about 2 mm each are typically used. A separation of about 0.5 mm between the image transmission elements provides a satisfactory depth or three-dimensional sensation, when the images are converted to electrical signals and displayed on a television monitor. This separation may be varied, however, so long as the light transmission elements do not touch.

The distal end 6 of the probe 4, as seen in FIG. 1, is terminated at an angle of about 25° to 30°. The elements 18 and 18, are terminated at the same angle as is the containing tube 20. As a result of the angles of these terminations, rotation of the arthroscope along its longitudinal axis allows the surgeon also to look off to the side. The instrument will view the region at a tilt of 25° to 30° from its longitudinal axis and the surgeon is not limited to a straight-ahead view.

This viewing angle could, however, vary from 0° (straight ahead) to 60°, for special applications, although a tilt of 25°-30° is more typical. Also, the tube 4 could be made flexible for some applications. The curvature of the tube might be changed during use by an internally located wire connected at one end to the distal end of the tube. Such curvature adjusting means are known.

The image transmission elements are shown in vertical alignment in FIG. 2, but this alignment obviously changes as the arthroscope is rotated in use. The ends of the image transmission elements are additionally oriented at a slight angle toward each other, so that the fields of view 22 and 24 of each converge at a distance of about 2.5 cm from their distal ends. Other distances of convergence may, however, be selected, depending on the use to which the instrument is put.

Illumination of the viewing region is provided by illuminating fiber bundles 26, which, in this embodiment, also extend through tube 20. Bundles 26 are optically coupled in a conventional manner to light entry port 16. Glass rods or other light transmitting elements could also be used.

Figure 3:
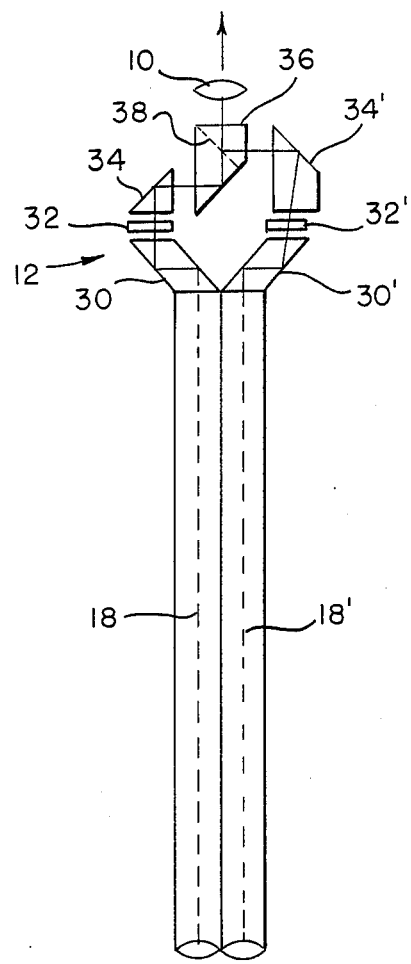
FIG. 3 is a longitudinal sectional view of the arthroscope used in this invention, including a prismatic arrangement for merging the images received from the distal end of each image transmission element.

FIG. 3 illustrates the parallel optical paths of the images transmitted by image transmitting elements 18 and 18, from their distal ends to the collimating element 10. These elements are each optically coupled to the prismatic arrangement 12, so that light from each element enters, respectively, the associated bottom face of parallelogram-shaped prisms 30 and 30,.

The optical path of each image can be opened and closed by shutters 32 and 32, In the embodiments of the invention illustrated in FIG. 3, these shutters remain continually open, or may be eliminated entirely. The shutters are needed for the embodiment of FIG. 4, however, and the presentation of three-dimensional images.

The images are transmitted to the bottom faces of triangular prism 34 and trapezoidal prism 34', respectively. Each of these prisms transmits the received image to trapezoidal prism 36, the images being directed perpendicularly to the longitudinal axis of the probe to enter prism 36. Prism 36 also functions as a split beam device, diagrammatically represented by dotted line 38.

This split beam prism 36 redirects the images from prisms 34 and 34' through a collimating means 10. The images, upon leaving prism 36, are projected along an optical path coinciding with the longitudinal axis of the probe 4. The prismatic arrangement, in this way, converts a binocular image, i.e. an image taken from two points of origin or two points of view within a body cavity, to a converging (monocular) image.

Optical systems for converting monocular to binocular (but not three-dimensional) images are known, for example, the Leitz lens system. The system of this invention, however, uses these known optical systems in a completely different way, i.e. by converting binocular to monocular images. The optical path of each image is, therefore, opposite or reversed from those in prior art systems.

It is critical for the surgeon to be continually aware of the orientation of the viewed region. The top view of the region, when examination or surgery begins, must remain at the top, and the bottom view must remain at the bottom. This requirement applies while the instrument is rotated as much as 360° to obtain a full view. In order to achieve this consistent "uprightness," both the prism and collimating lenses are fixed to rotate as a unit with the rotation of the arthroscope.

The foregoing explanation applies to use of the arthroscope as an optical instrument. It is also intended to be used as an electro-optical instrument, in which the image transmission elements provide images that are converted to electrical input signals for television viewing.

Figure 4:
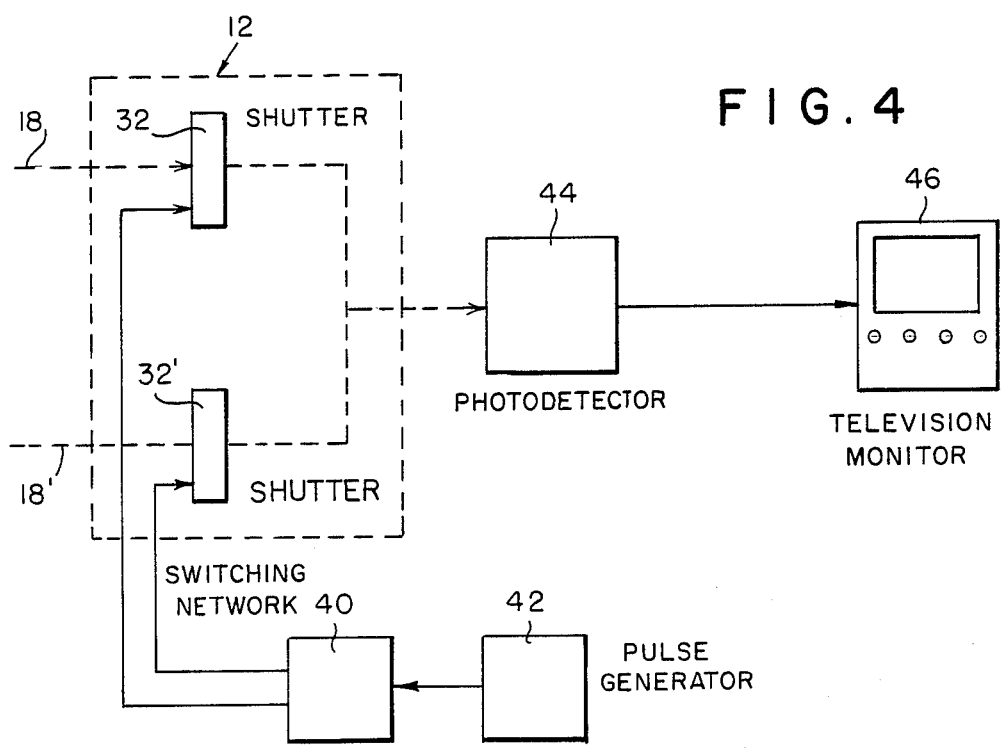
FIG. 4 is a schematic illustration of the elements and circuitry of this invention for producing from the output of an arthroscope a three-dimensional view on a standard television screen.

FIG. 4 schematically illustrates the operation of the shutters, the conversion of transmitted optical images to electrical pulses and the three-dimensional display on a television screen of images generated from these pulses. The creation of a three-dimensional display is explained in the above-mentioned United States patents to Jones ('587) and Jones et al ('328). As explained in these patents, the image or view to be depicted in three dimensions must be alternately presented on the television screen according to a particular sequence or pattern. The sequences in either of these patents are, in general, created by the alternate viewing of the image first from one point or origin and then from another. These points of origin are the distal ends of the image transmission elements.

The three-dimensional systems described in these two patents are collectively known as the "Visidep" system. In using the "Visidep" system, images from each point of origin are obtained by cameras positioned at these points. The shutters 32 and 32' serve the function of the two cameras in providing alternating or sequential images from two points of origin (the distal ends of elements 18 and 18'). The shutters need not be of any particular type, so long as they are capable of operating at a switching rate of from 8 to 15 times per second. Electro-optic, liquid crystal or mechanical shutters can be used.

To provide the needed images from different points of origin, the opening and closing of shutters 32 and 32' is controlled by a switching network 40. This switching network is, in turn, controlled by a pulse generator 42. Therefore, these system components serve the identical purpose as the corresponding components 14 and 16 in either of the two above-mentioned patents.

The optical images from each shutter are converted to electrical pulses by photodetector 44, which may be a charge-coupled device (CCD) or other device well known for this purpose. It replaces the collinating lens 10 illustrated in FIG. 3. The photodetector output is provided to a television monitor 46, on which the viewed region is displayed in three dimensions.

The use of a single photodetector, as compared to the two cameras used in the "Visidep" system, has advantages beyond instrument size reduction. Color and luminance imbalance, along with lens distortion, are minimized or eliminated. Also, the surgeon is able to rotate the instrument with one hand while viewing the region of surgery on the television screen. The surgeon's other hand is free to probe or perform surgery.

While particular embodiments of the present invention have been shown and described, it will, of course, be obvious to one skilled in the art that certain modifications can be achieved without departing from the spirit and concepts of the invention.

Although the invention has been described as an arthroscope, it should be apparent that it has application in all endoscopic devices, including gastroscopes, proctoscopes, laproscopes and cystoscopes. It should further be understood that the uses of the invention are not limited to medicine. It could be used, for example, to inspect the interior of tubing or pipes in a nuclear reactor or other devices or systems where disassembly is expensive or impractical.

What is claimed is:

1. A three-dimensional endoscopic viewing system, comprising;
    a probe having a distal end and a viewing end;
    a pair of image transmission elements positioned in parallel to each other within the probe, the elements extending from the viewing end of the probe to its distal end, the probe and image transmission elements at the distal end being terminated at an angle; whereby, upon rotating the probe, the image transmission elements transmit images of the entire region under observation to the viewing end of the instrument;
    prismatic means for receiving images from the viewing end of the light transmission elements and maintaining these images fixed in spatial orientation regardless of the rotational position of the probe;
    switching means for sequentially switching and transmitting the image received from each light transmission element; and
    means for converting these optical images to a three-dimensional visual display.

2. The endoscopic viewing system of claim 1, in which the angle of termination of the probe and light transmission elements is approximately 25° to 30°.

3. The endoscopic viewing system of claim 1, in which the angle of termination of the probe and image transmission elements is between 0° and 60°.

4. The endoscopic viewing system of claim 1, in which the lines of sight of the light transmission elements may be adjusted to converge at a predetermined distance.

5. The endoscopic viewing system of claim 4, in which the lines of sight of the light transmission elements at their distal ends converge at a distance of approximately 2.5 centimeters.

6. The endoscopic viewing system of claim 1, in which the prismatic means rotates with the rotation of the probe to maintain the viewed image upright.

7. The endoscopic viewing system of claim 1, further including shutters for sequentially transmitting images from each of the light transmission elements to the viewing system.

8. The endoscopic viewing system of claim 1, in which the light transmission elements comprise optic fiber bundles.

9. The endoscopic viewing system of claim 1 in which the image transmission elements comprise glass rods.

10. The endoscopic viewing system of claim 1, in which the probe comprises a flexible rod.

11. The endoscopic viewing system of claim 1, in which the shutters switch images from the light transmission elements at a frequency of from 8-15 times per second.

12. The endoscopic viewing system of claim 1, in which the optical image converting means includes a switching network for sequentially operating the shutters.

13. The endoscopic viewing system of claim 1, in which the optical images transmitted by the image transmission elements are converted to electric signals by a photoelectric element.

14. The endoscopic viewing system of claim 1, wherein the visual display means comprises a television monitor.

15. The endoscopic viewing system of claim 1, wherein the image transmission elements are each about 2 mm in diameter.

16. The method of creating three dimensional images on a television monitor, including the steps of:
  (a) providing an elongated probe having parallel arranged image transmission elements therein;
  (b) terminating the ends of the probe and the image transmission elements so that the optical axes of the elements are tilted between 25° and 30° from the longitudinal axis of the probe;
  (c) transmitting the optical images from each element to a prismatic system, whereby the simultaneous rotation of the probe and the prism system causes the optical images to remain in an upright orientation;
  (d) sequentially converting the images from each element to electrical signals according to a predetermined pattern of sequences; and
  (e) sequentially displaying the electrical signals on a visual display means to obtain a three-dimensional effect.

* * * * *